United States Patent [19]

Marchese et al.

[11] Patent Number: 5,061,480
[45] Date of Patent: Oct. 29, 1991

[54] TANNING COMPOSITION

[75] Inventors: Frank P. Marchese, Bronxville; Joseph S. Engenito, Jr., Elmont, both of N.Y.

[73] Assignee: Marchese Co., Inc., White Plains, N.Y.

[21] Appl. No.: 432,386

[22] Filed: Nov. 3, 1989

[51] Int. Cl.$^5$ .................... A61K 7/021; A61K 7/40; A61K 7/42; A61K 7/44
[52] U.S. Cl. ........................................ 424/59; 424/60; 424/63; 514/772; 514/773; 514/844; 514/847; 514/937; 514/938
[58] Field of Search ............................................ 424/59

[56] References Cited

U.S. PATENT DOCUMENTS 4,844,884 7/1989 Tur .................................... 424/59

FOREIGN PATENT DOCUMENTS 47-26687 7/1972 Japan .................................... 424/59

OTHER PUBLICATIONS

Sagarin, Cosmetics Science & Technology, 1957, pp. 1005–1008.
Gordon, P. R., et al., "Human Melanogenesis is Stimulated by Diacylglycerol", J. Invest Dermatol 93: 700–702, 1989.

Primary Examiner—Dale R. Ore

[57] ABSTRACT

A skin tanning and conditioning composition for accelerating the tanning process comprises specified nonionic surfactants together with tyrosine, protein hydrolysate and either riboflavin or adenosine triphosphate.

A method is also provided for preparing these compositions.

10 Claims, No Drawings

TANNING COMPOSITION

FIELD OF THE INVENTION

This invention relates to tanning and skin treatment compositions, and is particularly related to such compositions which enhance tanning of the skin.

The invention also relates to a method of accelerating the tanning of the skin using such compositions.

BACKGROUND OF THE INVENTION

Many compositions have heretofore been proposed for skin tanning and some are currently available commercially. It is generally accepted that tanning is caused by the ultra violet component of sunlight and that the degree of tanning of human epidermis by the sun rays depends upon the complexion of the individual. Also, while tanning of the skin is not fully understood, it is generally believed that it results from the formation of melanin, a skin pigment, migration of the melanin to the surface of the skin and its oxidation darkening (see U.S. Pat. No. 3,988,437).

The degree to which an individual is tanned upon exposure to sunlight or artificial sources of ultra violet light depends upon the duration, intensity and exposure to sunlight or such sources. The ultra violet energy which is absorbed by the skin can produce an erythemal reaction (redness) of the skin. Therefore, an attempt at getting a deeper or more intense tan by prolonged exposure to sunlight or other artificial sun sources can cause excessive redness or sunburn of the skin. In order to alleviate redness or sunburn of the skin, some tanning compositions include conventional sun protection ingredients or so-called "sun blockers", which filter out the ultra violet component of the sun rays. While the presence of such ingredients in the tanning composition offer some protection against erythemal reaction in the skin, it also prevents quick tanning because considerable portion of the ultra violet lights are filtered out by these ingredients. Thus, using tanning compositions containing sun blockers permit prolonged exposure to sun without the danger of sunburn, but the skin will not tan faster or deeper by the application of such compositions.

Several recent patents have disclosed various skin tanning compositions. For example, U.S. Pat. No. 3,988,437 issued Oct. 26, 1976 discloses a suntan composition which contains a fluorescent compound for protection against sunburn and to promote tanning.

U.S. Pat. No. 4,434,154 issued Feb. 28, 1984 discloses a tanning and ultra violet screening composition. The composition comprises dihydroxyacetone, octyldimethyl PABA, water oil and surfactant. The surfactants are sodium alkylsulfates wherein the alkyl group contains 8 to 16 carbon atoms.

U.S. Pat. No. 4,714,609 discloses a skin tanning composition comprising a vanillin as the active natural ingredient to accelerate the tanning process.

U.S. Pat. No. 4,781,914 issued Nov. 1, 1988 discloses a sunscreen and moisturizer composition containing polyglycerol-8-oleate for imparting moisture resistance or substantivity to the composition.

U.S. Pat. No. 4,783,332 issued Nov. 8, 1988 discloses a skin tanning composition comprising various ingredients including tyrosine or tyrosine precursor to panthenol and ethoxylated glycerides esterified with fatty acids as described therein.

In a paper published in 1987, Dr. Christine Jaworsky has disputed the claims of many producers of sun tan products who have claimed that their products contain active ingredients which accelerate the tanning process. So far as it is known, there is not available, at the present, a suitable tanning composition which satisfies the consumers' desire for quicker, deeper and more intense tan. See American Academy of Dermatology, Vol. 16 (1987), page 34.

It is therefore an object of this invention to provide a tanning composition which accelerates the skin tanning process.

It is also an object of this invention to provide such tanning compositions which promote and accelerate tanning of the skin without the need for prolonged exposure to harmful sun rays.

It is a further object of this invention to provide tanning compositions which produce a deeper and more intense tan of the skin rapidly and uniformly on the skin.

The foregoing and other advantageous features of the present invention will be more fully appreciated from the ensuing detailed description.

SUMMARY OF THE INVENTION

In accordance with this invention, a skin tanning and conditioning composition is provided which is capable of imparting intense, deep and more uniform tan quicker than the currently available suntan products. The composition comprises tyrosine as the active ingredient together with protein hydrolysate and riboflavin. Certain non-ionic surfactants are included in the composition in order to accelerate the tanning process so as to avoid prolonged exposure to sun rays or other sources of ultra violet radiation. The non-ionic surfactants used in the compositions of this invention to promote and accelerate the tanning process include polyoxyethylene 4 lauryl ether (Laureth 4) and sorbitan laurate, which are the preferred surfactants.

The method of preparation of the tanning compositions comprises mixing water at a temperature of from about 20° to about 30° C., with an aqueous concentrate containing tyrosine (or a derivative thereof), protein hydrolysate and riboflavin or adenosine triphosphate, and agitating the resulting mixture to obtain a homogeneous solution. The non-ionic surfactant is thereafter added to the solution and stirring continued. The final product has a smooth, creamy consistency.

The composition of this invention also comprises other conventionally employed ingredients such as a thickener, a biocide, cocoa butter, an emollient and a pH adjuster.

DETAILED DESCRIPTION OF THE INVENTION

The tanning compositions of the present invention contain a combination of active ingredients with a non-ionic surfactant which act in synergism to increase the rate of penetration of the active ingredients into the skin and therefore accelerate tanning on the epidermis. Moreover, the inclusion of the non-ionic surfactant in the composition of this invention produces a more uniform skin tan rather than spotty tans produced by using tanning compositions which do not contain such non-ionic surfactants.

The non-ionic surfactant which is particularly well suited in the practice of this invention is polyoxyethylene 4 lauryl ether which is available from ICI Americas, Inc., Wilmington, Delaware, and is sold under the trade name BRIJ 30. This surfactant is also referred to as laureth-4, which is its CTFA (Cosmetic Toiletry and Frangrance Association) adopted name. Other non-ionic surfactants of this type which can be used in this invention include polyoxyethylene 4 lauryl ether containing 0.01% butylated hydroxy anisole (BHA) and 0.005% citric acid as preservatives. This surfactant is also available from ICI Americas, Inc. and is also known by its CTFA adopted name of Laureth-4 and sold under the trade name BRIJ 30 SP. Still other non-ionic surfactants which are suitable in the compositions of this invention are: polyoxyethylene 23 lauryl ether, known by its CTFA adopted name of Laureth-23 (trade name BRIJ 35); polyoxyethylene 23 lauryl ether containing 0.01% BHA and 0.005% citric acid, known by its CTFA adopted name of Laureth-23 (trade name BRIJ 35 SP); polyoxyethylene 2 cetyl ether with 0.01% BHA and 0.005% citric acid, known by its CTFA adopted name of Ceteth-2 (trade name BRIJ 52); polyoxyethylene 10 cetyl ether with 0.01% BHA and 0.005% citric acid, known by its CTFA and adopted name of Ceteth-10 (trade name BRIJ 56); polyoxyethylene 20 cetyl ether with 0.01% BHA and 0.005% citric acid, known by its CTFA adopted name of Ceteth-20 (trade name BRIJ 58); polyoxyethylene 2 stearyl ether with 0.01% BHA and 0.005% citric acid, known by its CTFA name of Steareth-2 (trade name BRIJ 72); polyoxyethylene 10 stearyl ether with 0.001% BHA and 0.005% citric acid, known by its CTFA name of Steareth-10 (trade name BRIJ 76); polyoxyethylene-2 oleyl ether with 0.01% BHA and 0.005% citric acid, known by its CTFA name of Oleth-2 (trade name BRIJ 92); polyoxyethylene-2 oleyl ether (low color and odor) with 0.01% BHA and 0.005% citric acid, known by its CTFA name of Oleth-2 (trade name BRIJ 93); polyoxyethylene 10 oleyl ether with 0.01% BHA and 0.005% citric acid, known by its CTFA name of Oleth-10 (trade name BRIJ 96) and polyoxyethylene 10 Oleth ether (low color and odor) with 0.01% BHA and 0.005% citric acid, known by its CTFA name of Oleth-10 (trade name BRIJ 97).

The aforementioned non-ionic surfactants may be generally referred to as polyoxyethylene alkyl ethers and may be used alone or in admixture with one another.

Another type of non-ionic surfactants which may be used in the present invention is polyoxyethylene 20 sorbitan monolaurate, known by its CTFA name of Polysorbate-20 (trade name TWEEN 20) and polyoxyethylene 4 sorbitan monolaurate, known by its CTFA name of Polysorbitan-21 (trade name TWEEN 21), and other such polyoxyethylene derivatives of sorbitan fatty acid esters.

Other types of non-ionic surfactants which may be used in the composition of this invention are sorbitan fatty acid esters which include sorbitan monolaurate, known by its CTFA adopted name of Sorbitan Laurate (trade name ARLACEL 20); sorbitan monopalmitate, known by its CTFA adopted name of Sorbitan Palmitate (trade name ARLACEL 40); sorbitan monostearate, known by its CTFA adopted name of Sorbitan Stearate (trade name ARLACEL 60); sorbitan monooleate, known by its CTFA adopted name of Sorbitan Oleate (trade name ARLACEL 80); sorbitan sesquioleate, known by its CTFA adopted name of Sorbitan Sesquioleate (available under the trade names ARLACEL 83 and ARLACEL C); sorbitan trioleate, known by its CTFA adopted name of Sorbitan Trioleate (trade name ARLACEL 85); glycerol monstearate and polyoxyethylene stearate, known by its CTFA adopted name of Glycerl Stearate and PEG-100 Stearate (trade name ARLACEL 165); and glycerol monoleate diluted with propylene glycol and containing 0.02% BHA and 0.01% citric acid added as preservatives, known by its CTFA adopted name of Glycerl Oleate and Propylene Glycol (trade name ARLACEL 186).

All the trade names of the aforementioned surfactants are those of ICI Americas, Inc. Each one of said surfactants may be used alone or in combination with each other and/or one or more of the other surfactants of this invention.

The active tanning ingredient of the composition of this invention is tyrosine, an amino acid. Tyrosine and its derivatives are capable of penetrating the deeper layers of the skin when applied percutaneously and cause tanning of the skin when exposed to sunlight or ultra violet radiation. It is believed that the addition of small amount of riboflavin (vitamin B12) or adenosine triphosphate to the tyrosine accelerates the tanning process since riboflavin accelerates the oxidation process which produces the skin tanning pigment from tyrosine. In addition, riboflavin imparts a yellowish color to the resulting composition while adenosine triphosphate imparts a white color thereto.

In addition to tyrosine and riboflavin, the composition of this invention also includes collagen hydrolysates having molecular weight ranging from about 2000 to about 100,000.

A mixture of tyrosine, riboflavin and collagen hydrolysate manufactured by Induchem, Zurich, Switzerland is sold under the trade name UNIPERTAN 24. When it is desired to impart a white color to the resulting tanning composition, the riboflavin is replaced with adenosin triphosphate (ATP) and mixtures of tyrosine, collagen hydrolysate and adenosine triphosphate are available from Induchem and sold under the trade name UNIPERTAN 242.

The composition of this invention also includes cocoa butter which serves to protect the skin; dimethylpolysiloxane (Dimethicone-200 available from Dow Chemicals Co., Midland, Michigan) having a viscosity of from about 100 to about 1000 cps serving as moisturizer; a thickening agent such as polyacrylic acid sold under the trade name Carbomer by the B.F. Goodrich Company, a biocide such as imidazolidinyl urea (Germal II available from Sutton Laboratories, Chatham, New Jersey); methyl paraben, propyl paraben, tetrasodium ethylenediaminetetraacetate. (EDTA) used as water softener, triethanolamine to adjust the pH, a fragrance and water.

The method of preparation of the composition of this invention will be now illustrated by the following examples. It is to be understood, of course, that these examples are merely illustrative and should not be interpreted so as to limit the scope of the invention.

EXAMPLE 1

237.09 parts by weight of sterilized water was charged to a reaction vessel equipped with a stirrer at room temperature. 1.45 parts of polyacrylic acid thickener (Carbomer 934) was added slowly to the water in the reaction vessel and the contents were stirred vigorously for one hour to avoid clumping or agglomeration. A separate mixture containing 16.61 parts Laureth-4, 2.85 parts polysorbate-20, 12.87 parts cocoa butter, 0.72 part methyl paraben and 0.29 parts propyl paraben was heated to a temperature of 50°–60° C. to give a homogeneous solution and then, this mixture was added slowly to the reaction vessel with continued agitation until a homogeneous solution was obtained. Thereafter, the following ingredients were added sequentially with continued agitation:

8.56 parts Dimethicone-200 having a viscosity of 700 cps.

14.30 parts of aqueous concentrate containing 8.0 wt. % tyrosine, 21.0 wt. % protein hydrolysate and 0.3 wt. % riboflavin 0.86 part Germal II 0.86 part tetrasodium EDTA 3.82 parts triethanolamine (99%)

0.74 part fragrance

The resulting composition was a homogeneous yellow cream with a pH of about 6.5.

The composition of this example in parts by weight and weight percent is as follows:

| Ingredients | Parts by weight | Weight % |
| --- | --- | --- |
| Sterilized water | 237.09 | 78.90 |
| Carbomer 934 | 1.45 | 0.48 |
| Laureth-4 (BRIJ 30) | 16.61 | 5.53 |
| Polysorbate 20 | 2.85 | 0.95 |
| Cocoa butter | 12.82 | 4.28 |
| Methyl Paraben | 0.72 | 0.24 |
| Propyl Paraben | 0.29 | 0.10 |
| Dimethicone-200 (700 cps) | 8.56 | 2.85 |
| UNIPERTAN 24 | 14.30 | 4.76 |
| Germal II | 0.30 | 0.10 |
| Tetrasodium EDTA | 0.86 | 0.29 |
| Triethanolamine | 3.82 | 1.27 |
| Fragrance | 0.74 | 0.25 |
| TOTAL: | 300.46 | 100.00 |

EXAMPLE 2

The procedure in this example was the same as in Example 1 except that the non-ionic surfactant was sorbitan monolaurate (ARLACEL 20). Also, before adding triethanolamine and fragrance, Elastin (a protein fiber) and protein hydrolysate were added to the mixture to impart the desired color and consistency to the resulting composition. The formulation used in this example is as follows:

| Ingredients | Wt. % |
| --- | --- |
| Sterilized water | 62.78 |
| Carbomer 940 | 0.30 |
| ARLACEL 20 | 5.00 |
| Polysorbate | 2.00 |
| Cocoa butter | 4.50 |
| Methyl Paraben | 0.25 |
| Propyl paraben | 0.10 |
| Dimethicone-200 (700 cps) | 3.00 |
| UNIPERTAN 242 | 5.00 |
| GERMAL II | 0.30 |
| Tetrasodium EDTA | 0.30 |
| Elastin | 5.00 |
| Protein hydrolysate | 10.00 |
| Triethanolamine | 1.22 |
| Fragrance | 0.25 |
| TOTAL | 100.00 |

EXAMPLE 3

This example was similar to Example 1 except the UNIPERTAN 242 was used instead of UNIPERTAN 24. No Elastin or additional protein hydrolysate were included in the composition.

The formulation in this example is as follows:

| Ingredients | Wt. % |
| --- | --- |
| Sterilized water | 77.80 |
| Carbomer 934 | 0.30 |
| BRIJ 30 | 6.00 |
| Polysorbate-20 | 1.00 |
| Cocoa butter | 4.50 |
| Methyl paraben | 0.25 |
| Propyl paraben | 0.10 |
| Dimethicone-200 (700 cps) | 3.00 |
| UNIPERTAN | 5.00 |
| GERMAL II | 0.30 |
| Triethanolamine | 1.25 |
| Fragrance | 0.20 |
| TOTAL | 100.00 |

The amount of the non-ionic surfactant can vary from about 1 to about 10 weight percent based on the composition, and is preferably from about 4 to about 6 weight percent. Tyrosine is used in an amount varying from about 0.2 to about 0.5 weight percent and the amount of riboflavin or adenosin TPA is usually very small and is in the order of about 0.01-0.02 weight percent. The amount of protein hydrolysate varies from about 0.5 to about 1.5 weight percent. The amount of cocoa butter can vary from about 4 to about 8 weight percent and Dimethicone may be used in the amount of from about 1 to about 10 weight percent based on the total composition.

The remaining components, except water, are generally used in very small amounts in order to achieve their respective and known functions in the formulation such as, e.g., obtaining the desired viscosity, germicidal or biocidal property, moisturizing capability, etc. Sterilized water or deionized water constitutes the bulk of the formulation.

The resulting composition is water soluble with a yellow or white creamy consistency. It can be readily applied to the skin from the usual types and varieties of containers by simply squirting it from the container onto the skin and spreading it thereover by the hands. It is non-toxic, non-allergenic and, in addition to its quick tanning property, also conditions the skin by imparting smoother and spot-free texture thereto.

The composition of this invention was tested on selected individuals based on age, nature of skin and source of radiation as follows:

1. Fifty individuals (30 males and 20 females) age 20-65.
2. All individuals tested were caucasian having very light to medium skin.
3. The source of ultra violet radiation was natural sunlight and radiation lamps.
4. The tanning property of the composition was compared with other tanning products.

All individuals tested reported that the composition of this invention produced a faster tan than the available suntan products. Moreover, they reported that the present compositions prevented sunburn and left their skins smooth, with an even glow and a more intense tan over the entire area of their bodies to which they had applied the composition of this invention.

While the invention has heretofore been described with a certain degree of specificity, it is understood that some obvious modifications and changes may be made by those skilled in the art, both in the composition as well as the method of its preparation. Such changes and modifications are nevertheless within the contemplation of the present invention.

What is claimed is:

1. A skin tanning composition comprising from about 1 to about 10 weight percent non-ionic surfactant, from about 0.2 to about 0.5 weight percent tyrosine or a derivative of tyrosine, from about 0.5 to about 1.5 weight percent protein hydrolysate, and riboflavin or adenosine triphosphate, the balance being essentially water, wherein said non-ionic surfactant is selected from the group consisting of polyoxyethylene alkyl ethers, polyoxyethylene sorbitan fatty acid esters, and mixtures thereof.

2. A tanning composition as in claim 1 wherein said non-ionic surfactant is polyoxyethylene alkyl ether.

3. A tanning composition as in claim 2 wherein said non-ionic surfactant is polyoxyethylene 4 lauryl ether.

4. A tanning composition as in claim 1 wherein said non-ionic surfactant is polyoxyethylene sorbitan fatty acid ester.

5. A tanning composition as in claim 4 wherein said polyoxyethylene sorbitan fatty acid ester is polyoxyethylene sorbitan monolaurate.

6. A method for preparing a tanning composition having enhanced skin tanning capability which comprises mixing water with an aqueous concentrate containing from about 0.2 to about 0.5 weight percent tyrosine or a derivative of tyrosine, from about 0.5 to about 1.5 weight percent protein hydrolysate and riboflavin or adenosine triphosphate, at a temperature of from about 20° to about 30°, stirring the resulting mixture to obtain a homogeneous solution and thereafter adding from about 1 to about 10 weight percent of a non-ionic surfactant to said homogeneous solution with continued agitation to obtain a homogeneous creamy composition, wherein said non-ionic surfactant is selected from the group consisting of polyoxyethylene alkyl ethers, polyoxyethylene sorbitan fatty acid esters, and mixtures thereof.

7. A method as in claim 6 wherein said non-ionic surfactant is polyoxyethylene alkyl ether.

8. A method as in claim 7 wherein said non-ionic surfactant is polyoxyethylene 4 lauryl ether.

9. A method as in claim 1 wherein said non-ionic surfactant is polyoxyethylene sorbitan fatty acid ester.

10. A method as in claim 9 wherein said polyoxyethylene sorbitan fatty acid ester is polyoxyethylene sorbitan monolaurate.

* * * * *